Jan. 6, 1948. C. MALLERIN Plant Pat. 775
ROSE PLANT
Filed Nov. 4, 1942
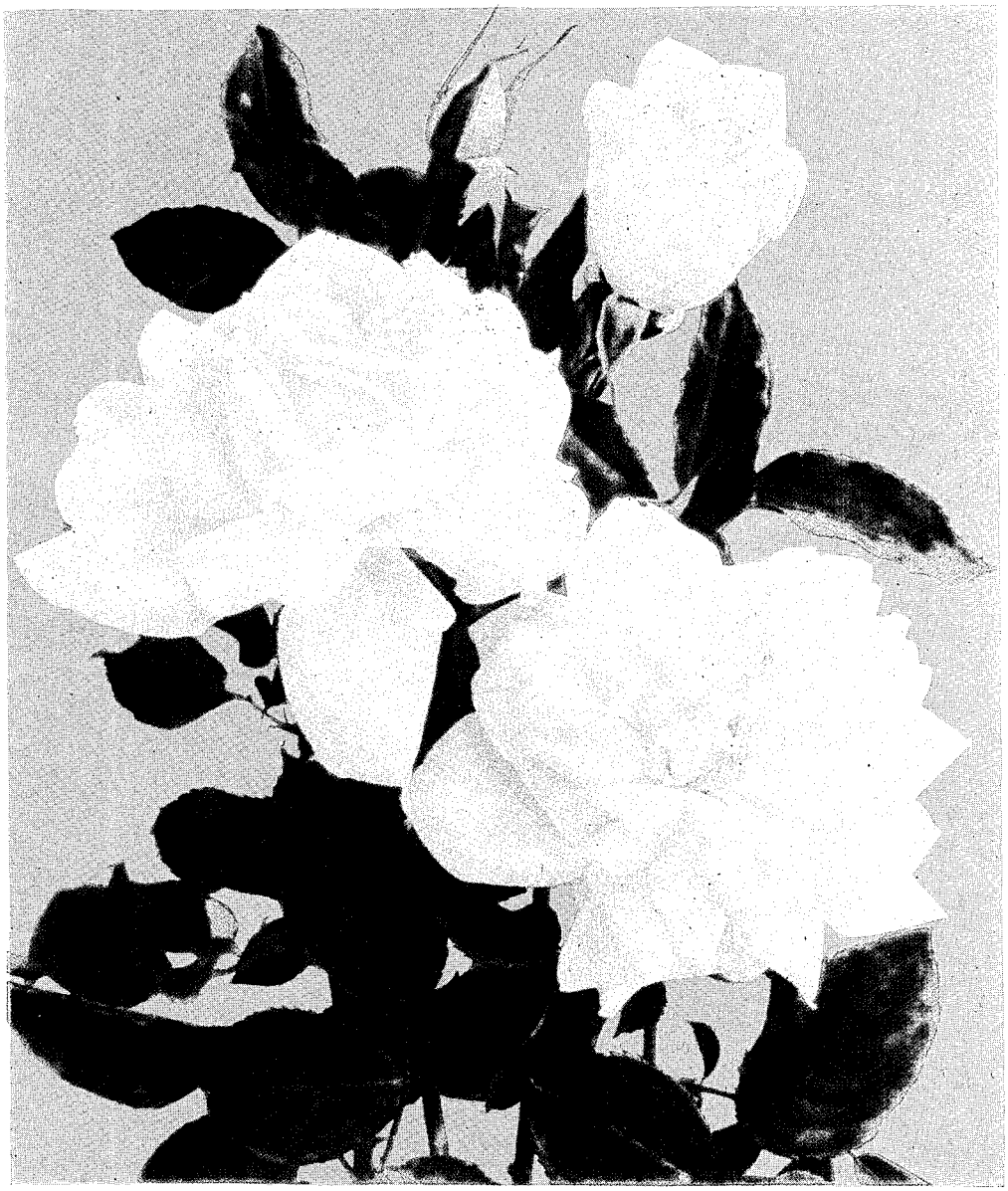
Inventor
Charles Mallerin
By Robb & Robb
Attorneys Patented Jan. 6, 1948

Plant Pat. 775

UNITED STATES PATENT OFFICE

775

ROSE PLANT

Charles Mallerin, Varces, France, assignor to Jackson & Perkins Company, Newark, N. Y., a corporation of New York Application November 4, 1942, Serial No. 464,557

1 Claim. (Cl. 47—61)

This invention relates to a new and distinct variety of rose plant, originating as the result of the crossing of two well known varieties "Soeur Therese" and "Feu Joseph Looymans."

This new variety shows a distinct advance in the development of new roses of the yellow color, and it is characterized as to novelty by the vigorous, tall and open growth of the bush on which the foliage is well spaced. The upright character of the growth of this new rose differs from the habit of its parent "Soeur Therese," and, in fact, differs from any other variety of which I am aware.

The new variety produces a symmetrical flower which unfolds perfectly to a full, open, almost flat shape. In respect to its color, it is noted that it is a shade of Yellow lying between Lemon Chrome and Empire Yellow and the reverse of Empire Yellow, which is unusual in this type of rose. These color tones remain throughout the entire life of the flower.

The flower is also distinct because of its large size and the fullness of the petals, together with the large number of petals which make the rose unusual and different from the existing varieties.

One of its valuable characteristics is its habit of exceptional continuity of blooming, which, together with the other features, make a very desirable and attractive rose.

The following is a detailed description of this new variety of rose, the color terminology herein employed being in accordance with Ridgway's Color Standard:

Parentage: Seedling.

*Seed parent.*—"Soeur Therese."

*Pollen parent.*—"Feu Joseph Looymans."

Classification: Botanic and commercial—Hybrid tea.

*Flower*

(Observations made in the morning of September 25, 1941, at Newark, New York.)

Blooming habit: Continuous.

Bud:

*Size.*—Large.

*Form.*—Ovoid. Is not affected by wet or hot weather.

*Color.*—When sepals first divide—Light Cadmium, Plate 4. When petals begin to unfurl—Light Cadmium, Plate 4, overlaid with Lemon Chrome, Plate 4. When half blown—inside of petals—between Lemon Chrome, Plate 4, and Empire Yellow, Plate 4. Reverse of petals—Empire Yellow, Plate 4.

*Sepals.*—Branched, "hood" above bud. Curl back when petals begin to unfurl. Color—outside—Oil Green, Plate 5; inside—Light Lumiere Green, Plate 17.

*Calyx.*—Shape—pear. Size—long. Aspect—smooth. Color—Lettuce Green, Plate 5.

*Peduncle.*—Length—medium. Aspect—rough. Color—Lettuce Green, Plate 5. Strength—stiff; slender.

*Opening.*—Bud opens well. Is not affected by adverse conditions.

Bloom:

*Size.*—Large. Average size when fully expanded, five inches.

*Borne.*—Singly.

*Stems.*—Medium length; strong.

*Form.*—When first open—cupped. Permanence—retains its form to the end.

*Petalage.*—Double (full but open center). Number of petals under normal conditions, 40.

*Color.*—Center of flower—Cadmium Yellow, Plate 3. Outer petals—Empire Yellow, Plate 4. Base of petals (aiglet)—Lemon Chrome, Plate 4. Inside of petals—between Lemon Chrome, Plate 4, and Empire Yelow, Plate 4. Reverse of petals—Empire Yelow, Plate 4. General tonality from a distance—Light Cadmium, Plate 4.

*Discoloration.*—General tonality at end of first day—Light Cadmium, Plate 4. Second day—between Lemon Chrome, Plate 4, and Empire Yellow, Plate 4. Third day—Empire Yellow, Plate 4.

Petals:

*Texture.*—Leathery. Is not affected by wet or hot weather.

*Appearance.*—Inside—satiny; outside—shiny.

*Form.*—Oval.

*Arrangement.*—Imbricated (regularly arranged shinglelike). Petaloids in center—few; small.

*Persistence.*—Drop off cleanly.

*Fragrance.*—Moderate. Nature—tea (average hybrid tea scent).

*Lasting quality.*—On the plant and as cut flower, long.

Genital organs:

*Stamens, anthers.*—Large; many. Color—Deep Chrome, Plate 3. Arrangement—regular around styles.

*Stamens, filaments (threads).*—Long. Color—Grenadine Red, Plate 2.

*Pollen.*—Light Orange Yellow, Plate 3.

*Styles.*—Columnar, medium, uneven length; heavy.
*Stigmas.*—Apricot Yellow, Plate 4.
*Ovaries.*—All enclosed in calyx.

*Plant*

Form: Bush.
Growth: Very vigorous; branching.
Foliage: Three to five leaflets.
*Size.*—Medium.
*Quantity.*—Abundant.
*Color.*—*New foliage*—upper side—Oil Green, Plate 5, overlaid with Van Dyke Red, Plate 13; under side—Van Dyke Red, Plate 13. *Old foliage*—upper side—Yew Green, Plate 31; under side—Light Cress Green, Plate 31.
*Shape.*—Oval pointed.
*Texture.*—Upper side—leathery; under side—rough. Ribs and veins—ordinary.
*Edge.*—Serrated (saw toothed).
*Serration.*—Single; small.
*Rachis.*—Cress Green, Plate 31. Under side—smooth.
*Stipules.*—Long; bearded.
*Disease resistance.*—Resistant, as determined by observation of the plant during its development in association with other varieties grown under comparable conditions.

Wood:
*New wood.*—Color—Rainette Green, Plate 31. Bark—smooth.
*Old wood.*—Color—Cress Green, Plate 31. Bark—smooth.
Thorns:
*Thorns.*—Quantity—on main stalks from base and on laterals from stalk—ordinary. Form—narrow base; short; hooked downward. Color when young—Hay's Russet, Plate 14. Position—irregular.
*Prickles.*—Quantity—on main stalks and on laterals—none.
*Short needles.*—Quantity—on main stalks and on laterals—none.

I claim:

A new and distinct variety of rose plant, characterized as to novelty by its vigorous, tall and open growth; the yellow color of its blossoms; the large size, symmetrical flowers unfolding perfectly to almost flat shape when fully open and comprising petals of large number; and the exceptional continuity of the blooms, substantially as shown and described.

CHARLES MALLERIN.